(12) United States Patent
Salimath et al.

(10) Patent No.: US 6,884,421 B2
(45) Date of Patent: Apr. 26, 2005

(54) PHARMACEUTICAL COMPOSITION FOR DIABETIC NEPHROPATHY

(75) Inventors: Paramahans Veerayya Salimath, Karnataka (IN); Kari Sambaiah, Karnataka (IN); Chikunda Dattatreya Nandini, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 347 days.

(21) Appl. No.: 10/113,887

(22) Filed: Mar. 27, 2002

(65) Prior Publication Data

US 2003/0185917 A1 Oct. 2, 2003

(51) Int. Cl.$^7$ .............................. A45F 5/00; F42B 39/02
(52) U.S. Cl. ................................................ 424/195.18
(58) Field of Search .................................... 424/195.18

(56) References Cited

U.S. PATENT DOCUMENTS 4,968,694 A * 11/1990 Madsen et al. ................ 514/23
5,789,393 A * 8/1998 Dressman et al. ............ 514/57

FOREIGN PATENT DOCUMENTS

JP 2002027941 * 12/2002 ............. A23L/1/22

OTHER PUBLICATIONS

Cameron–Smith, D et al., "Dietary Guar Gum Improves Insulin Sensitivity in Streptoszotocin–Induced Diabetic Rats," The Journ of Nutrition: Feb. 1997, 127, 2, pp. 359–364.*

Nandini, C. D. etal., "Effect of Dietary Fibre on Intestinal and Renal Disaccharidases in Diabetic Rats," Nutrition Research, Elsevier Science, 2000, vol. 20, No. 9, pp. 1301–1307.*

Kumar, C.M. et al., "Modulatory effect of butyric acid–a product of dietary fiber fermentation in experimentally induced diabetic rats," Journal of Nutritional Biochemistry 13, (2002) pp. 522–527.*

Chethankumar, M. et al., "Butyric acid modulates activities on intestinal and renal disaccharidases in experimentally induced diabetic rats," Nahrung/Food, 46 (2002) No. 5, pp. 345–348.*

Gallaher, D.D. et al., "Dietary guar gum halts further reanl enlargement in rats with established diabetes," Journal of Nutrition, 1992 Dec.;122(12):2391–2397.*

* cited by examiner

*Primary Examiner*—Patricia Leith
*Assistant Examiner*—Susan B. McCormick-Ewoldt
(74) *Attorney, Agent, or Firm*—Sughrue Mion, PLLC

(57) ABSTRACT

The present invention provides a synergistic pharmaceutical composition of butyric acid wheat fiber bran and guar gum and a method of treatment for diabetic nephropathy.

34 Claims, No Drawings

PHARMACEUTICAL COMPOSITION FOR DIABETIC NEPHROPATHY

FIELD OF INVENTION

The present invention relates to a synergistic pharmaceutical composition comprising butyric acid, insoluble wheat fibre bran and soluble guar gum and a method of treatment for Diabetic Nephropathy.

BACKGROUND AND PRIOR ART REFERENCES

Diabetic Nephropathy is one of the complications of diabetes mellitus involving basement membrane thickening as a result of reduction in Heparan Sulfate, Laminin and increase in type-IV Collagen. Diabetic Nephropathy is characterized by increased excretion of albumin in the urine as a result of Glomerular Basement Membrane damage. Glomeruli become more porous to passage of macromolecules. During Diabetic Nephropathy the functional unit of kidney, the Nephrons are damaged leading to increased filtration rate and also increased excretion of proteins in urine. Therefore, compositions helpful in modulating the damaged kidney membrane have a tremendous scope in preventing the progression of Diabetic Nephropathic state.

Diet plays a major role in management of diabetic complications. Dietary fibre—unabsorbable carbohydrates in the diet has many beneficial effects including slowing macromolecular digestion, slow release and absorption of glucose etc. The dietary fibres are fermented by microbes in the colon to short chain fatty acids and the role of butyric acid—a four carbon fatty acid in particular, on various physiological functions is receiving great attention.

A reference can be made to U.S. Pat. No. 6,248,375 wherein designed solid matrix nutritional product is designed containing dietary fibre and indigestible oligosaccharides to be administered to diabetics. The draw back of this nutritional product is that it does not include butyric acid, which is recognized for its role at the molecular level.

A reference can be made to U.S. Pat. No. 4,598,081 wherein a butyric acid analogue has been recommended for the treatment of complications of diabetes mellitus. The draw back is non-usage of dietary fibre, which acts as a reservoir of butyric acid and has supplementary beneficial effect.

A reference can be made to U.S. Pat. No. 6,303,586 wherein a supportive therapy in the form of stabilized rice bran is given in the treatment of diabetes. This includes both the solubilised and insolubilised fractions of the stabilized rice bran. The draw back of this therapy is that it includes only a single type of dietary fibre (rice bran).

A reference may be made to U.S. Pat. No. 6,303,174 that concerns with the food composition including resistant starch. The draw back of this composition is that it can include only a soluble fibre from grains and legumes.

A reference can be made to U.S. Pat. No. 6,248,390 wherein fibre-water-water containing soluble fibre is invented. The draw back of this invention is that it includes only water-soluble fibre.

Hence, a pharmaceutical composition comprising butyric acid, wheat bran and guar gum has a significant role in ameliorating the increased Glomerular Filtration Rate and protein in urine and also prevent the progression of Diabetic Nephropathy.

OBJECTS OF THE INVENTION

The main object of the present investigation is to provide a pharmaceutical composition comprising butyric acid, wheat bran and guar gum for treating Diabetic Nephropathy.

An object of the present invention is to provide a pharmaceutical composition to reduce albumin excretion and ameliorate the Glomerular Filtration Rate.

Yet another object of the present invention is to provide a pharmaceutical composition that provides a constant reservoir of butyric acid.

Further object of the present invention is to provide a soluble fibre guar, which is a hypoglycemic agent.

SUMMARY OF THE INVENTION

Accordingly the present invention provides a synergistic pharmaceutical composition useful for diabetic nephropathy comprising butyric acid, wheat bran and guar gum. The present invention also provides a method for the treatment of diabetic nephropathy.

DETAILED DESCRIPTION OF THE INVENTION

Accordingly, the present invention provides a synergistic pharmaceutical composition for the treatment of diabetic nephropathy in subjects, said composition comprising an effective amount of:

(a) butyric acid 1–1000 mg/kg body weight;

(b) an insoluble wheat fibre bran 1–5%;

(c) a soluble hypoglycemic agent guar gum fibre 1–2.5%; and (d) optionally pharmaceutically accepted additives.

An embodiment of the present invention, wherein the preferred dosage of said composition is in the range of 250–750 mg/kg body weight.

Yet another embodiment of the present invention, wherein the most preferred dosage of said composition is 500 mg/kg body weight.

Still another embodiment of the present invention, wherein the sustained release of butyric acid of said composition is effective in the treatment of diabetic nephropathy.

Further embodiment of the present invention, wherein the insoluble fibre wheat bran of said composition gets fermented all along the intestinal tract and acts a reservoir of butyric acid.

Yet another embodiment of the present invention, wherein said composition is effective in reducing Glomerular Filtration Rate.

Still another embodiment of the present invention, wherein said composition is effective in reducing urinary protein excretion.

Yet another embodiment of the present invention, wherein said composition is used for the prevention, treatment and control of diabetic nephropathy.

Further another embodiment of the present invention, wherein the pharmaceutically accepted additives are selected from group consisting of stearates and carbonates of magnesium, calcium and potassium.

Yet another embodiment of the present invention, wherein the subject is selected from mammals.

The present invention also provides a method of treating diabetic nephropathy in subjects with synergistic pharmaceutical composition, said composition comprising an effective amount of:

(a) butyric acid 1–1000 mg/kg body weight;

(b) an insoluble wheat fibre bran 1–5%;

(c) a soluble hypoglycemic agent guar gum fibre 1–2.5%; and (d) optionally pharmaceutically accepted additives.

An embodiment of the present invention, wherein the preferred dosage of said composition is in the range of 250–750 mg/kg body weight.

Yet another embodiment of the present invention, wherein the most preferred dosage of said composition is 500 mg/kg body weight.

Still another embodiment of the present invention, wherein the sustained release of butyric acid is effective in diabetic nephropathy.

Further another embodiment of the present invention, wherein the insoluble fibre wheat bran gets fermented all along the intestinal tract and acts a reservoir of butyric acid.

Still another embodiment of the present invention, wherein said composition is effective in reducing Glomerular Filtration Rate.

Yet another embodiment of the present invention, wherein said composition is effective in reducing urinary protein excretion.

Further embodiment of the present invention, wherein said composition is used for the prevention, treatment and control of diabetic nephropathy.

Still another embodiment of the present invention, wherein the pharmaceutically accepted additives are selected from group consisting of stearates and carbonates of magnesium, calcium and potassium.

Yet another embodiment of the present invention, wherein said composition reduces the Glomerular filtration rate (GFR) from about 15 mL/min to about 8 mL/min.

Still another embodiment of the present invention, wherein said composition reduces urinary protein from about 118 mg/24 hours to 88 mg/24 hours.

Yet another embodiment of the present invention, wherein the subject is selected from mammals.

The following examples are given by the way of illustration of the present invention and therefore should not be construed to limit the scope of the present invention

EXAMPLE 1

Diabetes is induced in Male Wistar rats weighing between 120 g using streptozotocin at 55 mg/kg body weight and the rats are fed with wheat bran (1 to 5%), guar gum (1 to 2.5%) and butyric acid in the range of 1, 2, 4, 6, 8 and 10 mg/kg body weight/day in the diet. After 4 days measurement of fasting blood glucose level in the plasma and urinary sugar levels assessed the diabetic status.

Fasting blood glucose level is measured in the plasma collected from retro-orbital plexus of the rats by glucose oxidase method. The reaction mixture is incubated for 15 minutes and absorbance is measured at 520 nm. Urinary sugar levels are measured by Dinitrosalicylic acid method. The reaction mixture is kept in boiling water bath for 10 minutes and the colour developed is measured at 540 nm.

Urinary creatinine is estimated by alkaline picrate reagent method. The reaction mixture is incubated at room temperature for 15 minutes and absorbance is measured at 520 nm. The plasma is deproteinsed using tungstic acid prior to creatinine estimation.

The Glomerular Filtration Rate is determined at the end of fifth week by measuring urinary creatinine and plasma creatinine. The formula used is $$\frac{\text{Urinary creatinine(mg/dL)} \times \text{Urine volume (mL)} \times 1000 \text{ (g)}}{\text{Plasma creatinine (mg/dL)} \times \text{Body weight (g)} \times 1440 \text{ (min)}} = \text{mL/min}$$

Urinary protein is determined at the end of fifth week by TCA precipitation method and the absorbance is measured at 660 nm.

The increased levels of fasting blood glucose, urinary sugar and urinary volume are reduced to a considerable extent. The progression of Diabetic Nephropathic state is considerably prevented by reducing the Glomerular Filtration Rate and urinary protein with the composition involving butyric acid, wheat bran and guar gum.

EXAMPLE 2

Diabetes is induced in Male Wistar rats weighing between 120 g using streptozotocin at 55 mg/kg body weight and the rats are fed with wheat bran (1 to 5%), guar gum (1 to 2.5%) and butyric acid in the range of 1, 2, 4, 6, 8 and 10 mg/kg body weight/day in drinking water. After 4 days measuring fasting blood glucose level in the plasma and urinary sugar levels assessed the diabetic status.

Fasting blood glucose level is measured in the plasma collected from retro-orbital plexus of the rats by glucose oxidase method. The reaction mixture is incubated for 15 minutes and absorbance is measured at 520 nm. Urinary sugar levels are measured by Dinitrosalicylic acid method. The reaction mixture is kept in boiling water bath for 10 minutes and the colour developed is measured at 540 nm.

Urinary creatinine is estimated by alkaline picrate reagent method. The reaction mixture is incubated at room temperature for 15 minutes and absorbance is measured at 520 nm. The plasma is deproteinsed using tungstic acid prior to creatinine estimation.

The Glomerular Filtration Rate is determined at the end of fifth week by measuring urinary creatinine and plasma creatinine. The formula used is $$\frac{\text{Urinary creatinine(mg/dL)} \times \text{Urine volume (mL)} \times 1000 \text{ (g)}}{\text{Plasma creatinine (mg/dL)} \times \text{Body weight (g)} \times 1440 \text{ (min)}} = \text{mL/min}$$

Urinary protein is determined at the end of fifth week by TCA precipitation method and the absorbance is measured at 660 nm.

The increased levels of fasting blood glucose, urinary sugar and urinary volume are reduced to a considerable extent. The progression of Diabetic Nephropathic state is considerably prevented by reducing the Glomerular Filtration Rate and urinary protein with the composition involving butyric acid, wheat bran and guar gum.

EXAMPLE 3

Diabetes is induced in Male Wistar rats weighing between 120 g using streptozotocin at 55 mg/kg body weight and the rats are fed with wheat bran (1 to 5%), guar gum (1 to 2.5%) and butyric acid in the range of 250, 500 and 750 mg/kg body weight/day in the diet. After 4 days measuring fasting blood glucose level in the plasma and urinary sugar levels assessed the diabetic status.

Fasting blood glucose level is measured in the plasma collected from retro-orbital plexus of the rats by glucose oxidase method. The reaction mixture is incubated for 15 minutes and absorbance is measured at 520 nm. Urinary sugar levels are measured by Dinitrosalicylic acid method. The reaction mixture is kept in boiling water bath for 10 minutes and the colour developed is measured at 540 nm.

Urinary creatinine is estimated by alkaline picrate reagent method. The reaction mixture is incubated at room temperature for 15 minutes and absorbance is measured at 520 nm. The plasma is deproteinsed using tungstic acid prior to creatinine estimation.

The Glomerular Filtration Rate is determined at the end of fifth week by measuring urinary creatinine and plasma creatinine. The formula used is $$\frac{\text{Urinary creatinine(mg/dL)} \times \text{Urine volume (mL)} \times 1000 \text{ (g)}}{\text{Plasma creatinine (mg/dL)} \times \text{Body weight (g)} \times 1440 \text{ (min)}} = \text{mL/min}$$

Urinary protein is determined at the end of fifth week by TCA precipitation method and the absorbance is measured at 660 nm.

The increased levels of fasting blood glucose, urinary sugar and urinary volume are reduced to a considerable extent. The progression of Diabetic Nephropathic state is considerably prevented by reducing the Glomerular Filtration Rate and urinary protein with the composition involving butyric acid, wheat bran and guar gum.

EXAMPLE 4

Diabetes is induced in Male Wistar rats weighing between 120 g using streptozotocin at 55 mg/kg body weight and the rats are fed with wheat bran (1 to 5%), guar gum (1 to 2.5%) and butyric acid in the range of 250, 500 and 750 mg/kg body weight/day in drinking water. After 4 days measuring fasting blood glucose level in the plasma and urinary sugar levels assessed the diabetic status.

Fasting blood glucose level is measured in the plasma collected from retro-orbital plexus of the rats by glucose oxidase method. The reaction mixture is incubated for 15 minutes and absorbance is measured at 520 nm. Urinary sugar levels are measured by Dinitrosalicylic acid method. The reaction mixture is kept in boiling water bath for 10 minutes and the colour developed is measured at 540 nm.

Urinary creatinine is estimated by alkaline picrate reagent method. The reaction mixture is incubated at room temperature for 15 minutes and absorbance is measured at 520 nm. The plasma is deproteinsed using tungstic acid prior to creatinine estimation.

The Glomerular Filtration Rate is determined at the end of fifth week by measuring urinary creatinine and plasma creatinine (Table 1).

TABLE 1

Effect of butyric acid on Glomerular filtration Rate in control and diabetic rats

| Groups | GFR (mL/min) |
|---|---|
| SFC | 2.87 ± 0.31 |
| SFD | 16.53 ± 1.48[a] |
| SFD-250 | 15.99 ± 1.30 |
| SFD-500 | 15.60 ± 1.21 |
| SFD-750 | 15.23 ± 1.04 |
| FFC | 2.65 ± 0.61 |
| FFD | 14.98 ± 1.63[b] |
| FFD-250 | 10.56 ± 1.05[b] |
| FFD-500 | 9.23 ± 1.09[b] |
| FFD-750 | 11.64 ± 1.27[b] |

Groups with numbers (eg. SFD-250) represent mg of butyric acid fed/kg body weight/day
SFC - Starch fed control
SFD - Starch fed diabetic
FFC - Fibre fed control
FFD - Fibre fed diabetic
Values are mean ±SEM of 6 rats in control and 14 rats in diabetic groups.
[a]Statistically significant compared to SFC at p < 0.05
[b]Statistically significant compared to SFD at p < 0.05

The formula used is $$\frac{\text{Urinary creatinine(mg/dL)} \times \text{Urine volume (mL)} \times 1000 \text{ (g)}}{\text{Plasma creatinine (mg/dL)} \times \text{Body weight (g)} \times 1440 \text{ (min)}} = \text{mL/min}$$

Urinary protein is determined at the end of fifth week by TCA precipitation method and the absorbance is measured at 660 nm (Table 2).

TABLE 2

Effect of butyric acid on urinary protein excretion in control and diabetic rats

| Groups | Urinary protein (mg/24 h) |
|---|---|
| SFC | 11.45 ± 1.28 |
| SED | 140.82 ± 11.47[a] |
| SFD-250 | 126.77 ± 9.82 |
| SFD-500 | 124.86 ± 6.81[b] |
| SFD-750 | 115.37 ± 10.91 |
| FFC | 12.16 ± 3.29 |
| FFD | 118.47 ± 12.41[b] |
| FFD-250 | 104.07 ± 11.31[b] |
| FFD-500 | 88.82 ± 9.82[b] |
| FFD-750 | 90.37 ± 9.14[b] |

Abbreviations as in Table 1

The increased levels of fasting blood glucose, urinary sugar and urinary volume are reduced to a great extent. The progression of Diabetic Nephropathic state is significantly prevented by reducing the Glomerular Filtration Rate and urinary protein with the composition involving butyric acid, wheat bran and guar gum.

Advantages

1. A synergistic pharmaceutical composition for treating Diabetic Nephropathy helps in preventing complications of diabetes.
2. A synergistic pharmaceutical composition for treating Diabetic Nephropathy by reducing the Glomerular Filtration Rate.
3. A synergistic pharmaceutical composition for treating Diabetic Nephropathy by reducing the urinary protein excretion.

What is claimed is:

1. A pharmaceutical composition comprising:
   (a) butyric acid;
   (b) an insoluble wheat bran fibre; and
   (c) guar gum fibre as a soluble hypoglycemic agent.
2. The pharmaceutical composition according to claim 1, wherein said composition is administered to a subject at a dose in the range of 250–750 mg/kg body weight.
3. The pharmaceutical composition according to claim 1, wherein said composition is administered to a subject at a dose of 500 mg/kg body weight.
4. The pharmaceutical composition according to claim 1, wherein butyric acid is released from said composition in a sustained manner, and is effective in the treatment of diabetic nephropathy.
5. The pharmaceutical composition according to claim 1, wherein the insoluble wheat bran fibre gets fermented all along the intestinal tract and acts a reservoir of butyric acid.
6. The pharmaceutical composition according to claim 1, wherein said composition is effective in reducing Glomerular Filtration Rate.
7. The pharmaceutical composition according to claim 1, wherein said composition is effective in reducing urinary protein excretion.

8. The pharmaceutical composition according to claim 1, wherein said composition is effective for treatment and control of diabetic nephropathy.

9. The composition according to claim 1, further comprising pharmaceutically accepted additive selected from group consisting of stearates and carbonates of magnesium, calcium and potassium.

10. The composition according to claim 1, wherein said composition is administered to a mammal.

11. A method of treating diabetic nephropathy in a subject, comprising administering the pharmaceuticals composition according to claim 1 to said subject.

12. The method according to claim 11, wherein said composition is administered to said subject at a dose in the range of 250–750 mg/kg body weight.

13. The method according to claim 11, wherein said composition is administered to said subject at a dose 500 mg/kg body weight.

14. The method according to claim 11, wherein butyric acid is released from said composition in a sustained manner and is effective in the treatment of diabetic nephropathy.

15. The method according to claim 11, wherein the insoluble wheat bran fibre gets fermented all along the intestinal tract and acts a reservoir of butyric acid.

16. The method according to claim 11, wherein said composition is effective in reducing Glomerular Filtration Rate.

17. The method according to claim 11, wherein said composition is effective in reducing urinary protein excretion.

18. The method according to claim 11, wherein said composition is effective for treatment and control of diabetic nephropathy.

19. The method according to claim 11, wherein the pharmaceutical composition further comprises a pharmaceutically accepted additive selected from the group consisting of stearates and carbonates of magnesium, calcium and potassium.

20. The method according to claim 11, wherein said method is effective in reducing the Glomerular Filtration Rate (GFR) from about 13–15 mL/min to about 8–9 mL/min.

21. The method according to claim 11, wherein said method is effective in reducing urinary protein from about 110–120 mg/24 hours to 80–90 mg/24 hours.

22. The method according to claim 11, wherein the subject is a mammal.

23. The method according to claim 11, wherein butyric acid is administered in the range of 1–1000 mg/kg body weight/day.

24. A method for reducing Glomerular Filtration Rate in a subject, in need there of comprising administering the pharmaceutical composition according to claim 1 to said subject.

25. A method for reducing urinary protein excretion in a subject, comprising administering the pharmaceutical composition according to claim 1 to said subject.

26. The pharmaceutical composition according to claim 1, wherein said insoluble wheat bran fibre is present in an amount of 1–5% by weight.

27. The pharmaceutical composition according to claim 1, wherein said guar gum fibre is present in an amount of 1–2.5% by weight.

28. A method of treating diabetic nephropathy in a subject, comprising administering in combination to said subject: butyric acid 1–1000 mg/kg body weight/day, an insoluble wheat bran fibre, and guar gum fibre as a soluble hypoglycemic agent.

29. The method according to claim 28, wherein butyric acid is administered to said subject in the range of 250–750 mg/kg body weight/day.

30. The method according to claim 28, wherein butyric acid is administered to said subject at a dose of 500 mg/kg body weight/day.

31. The method according to claim 28, wherein insoluble wheat bran fibre is administered in an amount of 1–5% by weight.

32. The method according to claim 28, wherein guar gum fibre is administered in an amount of 1–2.5% by weight.

33. The method according to claim 28, wherein said method reduces the Glomerular Filtration Rate (GFR) in said subject from about 13–15 mL/min to about 8–9 mL/min.

34. The method according to claim 28, wherein said method reduces urinary protein in said subject from about 110–120 mg/24 hours to 80–90 mg/24 hours.

* * * * *

UNITED STATES PATENT AND TRADEMARK OFFICE
CERTIFICATE OF CORRECTION

PATENT NO. : 6,884,421 B2
DATED : April 26, 2005
INVENTOR(S) : Paramahans Veerayya Salimath et al.

It is certified that error appears in the above-identified patent and that said Letters Patent is hereby corrected as shown below:

Title page,
Item [75], Inventors, delete "Chikunda Dattatreya Nandini" and insert -- Chilkunda Dattatreya Nandini --.

Signed and Sealed this

Twentieth Day of September, 2005

JON W. DUDAS
*Director of the United States Patent and Trademark Office*